United States Patent
Zhu (10) Patent No.: US 6,245,890 B1
(45) Date of Patent: Jun. 12, 2001

(54) PORCINE PROTEIN AND USES THEREOF

(75) Inventor: Alex Zhu, New York, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/277,391

(22) Filed: Mar. 26, 1999

(51) Int. Cl.$^7$ .............................. A61K 39/00; C07K 2/00
(52) U.S. Cl. ................ 530/350; 424/184.1; 424/185.1; 530/300
(58) Field of Search .............................. 424/184.1, 185.1; 530/350, 300

(56) References Cited

PUBLICATIONS

Macchiarini et al. J. Thoracic and Cardiovascular Surgery 116:831–843, 1998.*
Satake et al Clinical Transplantation 7(3):281–288, 1998.*
Aspeslet et al. Xenotransplantation 3:1–10, 1998.*
Doring, et al., Clinical Xenotransplantation of Solid Organs, The Lancet 1997, 349:867–871.
Taniguchi, et al., In Vivo Immunoadsorption of Antipig Antibodies in Baboons using a Specific Gal α1–3Gal Column, Transplantation 1996, 62(10):1379–1384.
Osman, et al., Combined Transgenic Expression of α–Galactosidase and α1,2–Fucosyltransferase Leads to Optimal Reduction in the Major Xenoepitope Gal α(1, 3)Gal, Proc. Natl. Acad. Sci. (USA) 1997, 94:14677–14682.
Zaidi, et al., Life–Supporting Pit–To–Primate Renal Xenotransplantation Using Genetically Modified Donors, Transplantaton, 65 (12):1584–1590. (1998).
Lin, et al., The Role of Antibodies in Acute Vascular Rejection of Pig–to–Baboon Cardiac Transplants, J. Clin. Invest. 1998, 101(8):1745–1756.
Cooper, Xenoantigens and Xenoantibodies, Xenotransplantation 1998, 5:6–17.
Hudson, Recombinant Antibody Fragments, Current Opinion in Biotechnology 1998, 9:395–402.
Begent, et al., Single–chair Fv Antibodies for Targeting Cancer Therapy, Biochemical Society Transactions 1997, 25(2):1007–1009.
MacLaren, et al., Variation in Porcine Red Blood Cell α–Galactosyl Expression and Agglutination by HJuman Serum, Transplant Proc. 1998, 30:2468.
Hinchliffe, et al., Molecular Cloning and Functional Characterization of the Pig Analogue of CD59: Relevance to Xenotransplantation1, J. Immunol. 1998, 160(8):3924–32.
Gautreau, et al., Human Natural Cytotoxic Antibodies Recognize Cross–Reactive Antigens on Pig Endothelial Cells and Pig Red Blood Cells, Transplant Proc. 1994, 26(3):1397.
Yang, et al., Xenoantigens Expressed on Swine Erthrocytes, Lymphoblastoid Cells, and Endothelial Cells, Transplant Proc. 1992, 24(2):593–4.
Platt, et al., Porcine Platelet Antigens Recognized by Human Xenoreactive Natural Antibodies, Transplantation 1994, 57(3):327–335.
Holzknecht, et al., Identification of Porcine Endothelial Cell Membrane Antigens Recognized by Human Xenoreactive Natural Antibodies, J. Immunol. 1995, 154(9):4565–75.
Tuso, et al., Pig Aortic Endothelial Cell Antigens Recognized by Human IgM Natural Antibodies, Transplantation 1993, 56(3):651–655.

* cited by examiner

*Primary Examiner*—David Saunders
*Assistant Examiner*—Amy DeCloux
(74) *Attorney, Agent, or Firm*—Amster, Rothstein & Ebenstein (57) ABSTRACT

The present invention provides a porcine antigen that binds to human xenoreactive antibodies. The porcine antigen differs from the known porcine xenoantigens in that the antigen does not include an αGal epitope. The present invention also provides methods to purify the porcine antigen of the invention, as well as agents that bind to the antigen. The antigen may be used to generate antibodies against the antigen. The antigen is useful for detecting the presence of human xenoreactive antibodies against the antigen in blood and blood compositions, and antibodies against the antigen may be used to detect the presence of the antigen in samples. The invention also provides methods and pharmaceutical compositions for reducing a host rejection response to a porcine xenograft. Finally, a method to treat human blood or blood-derived compositions to reduce the level of human xenoantibodies is disclosed.

1 Claim, 8 Drawing Sheets

PORCINE PROTEIN AND USES THEREOF

FIELD OF THE INVENTION

The present invention relates to a novel porcine protein that is involved in xenograft rejection in humans. Specifically, the present invention relates to a porcine protein, found in porcine red blood cells, that binds to human serum antibodies involved in xenograft rejection, but which does not bind to human serum antibodies against the dominant xenograft rejection antigen, namely, the αGal epitope. The present invention also relates to methods for the detection, isolation and use of the porcine red blood cell protein, as well as methods for the detection, isolation and use of human serum antibodies that bind to the protein. Finally, pharmaceutical compositions and methods of treatment are also provided.

BACKGROUND OF THE INVENTION

Organ transplantation has become the treatment of choice for various diseases associated with organ failure (Platt J L (1998) Nature 392:11–17; Auchincloss H Jr, and Sachs D H (1998) Ann Rev Immunol 16:433–70). However, the supply of organs from organ donors falls far short of meeting the rapidly increasing demand (Hammer C, Linke R, Wagner F, and Diefenbeck M (1998) Int Arch Allergy Immunol 116:5–21). In the United States, only 5% of the patients on various waiting lists for organ transplants ever receive the appropriate organs. One attractive approach to overcoming this shortage is to use animals as a source of organs for transplantation (Greenstein J L and Sachs D H (1997) Nat Biotechnol 15:235–238). The transplantation of organs or cells between members of different species is called xenotransplantation. Non-human primates are the closest biological relatives of human beings; therefore, their organs are most similar to humans, anatomically, physiologically and biochemically. In fact, organs from chimpanzees and baboons have been shown in clinical studies to exhibit extended xenograft survival following rather simple immunosuppression procedures (Bailey L L, Nehlsen-Cannarella S L, Concepcion W, and Jolley W B (1985) JAMA 254(23):3321–3329; Starzl T, Marchioro T L, and Peters G (1964) Transplantation 2:752–776). However, the large-scale production of these endangered non-human primates for the purpose of securing organs for transplantation is considered unethical and socially unacceptable (Cortesini R (1998) Transplant Proc 30(5):2463–2464). Furthermore, the transmission of pathogens from primates to humans is well documented, and pathogen-free primates are extremely difficult to raise (Allan J S (1995) Nat Medicine 2(1):18–21). In addition, a significant obstacle to the widespread adoption of xenotransplantation is the immunological incompatibility between nonprimate animals and humans, which results in strong host rejection responses to the xenotransplanted organ. Overcoming these host rejection responses is essential to enable widespread use of nonprimate animal organs in xenotransplantation.

The first immune barrier to xenograft survival is hyperacute rejection, which may occur within minutes after revascularization of an organ (Rosenberg J C, Hawkins E, and Rector F (1971) Transplantation 11(2):151–157). The rejection is induced by the activation of the host (recipient) complement cascade upon the binding of recipient xenoreactive natural antibodies to the xenograft. The major xenograft antigen (or "xenoantigen") responsible for the hyperacute rejection response has been identified as a carbohydrate epitope, Galα1,3Galβ1,4GlcNAc (referred to herein as "the αGal epitope"). The αGal epitope forms glycoconjugates on the cell surface of animal organs and cells (Thall A, and Galili U (1990) Biochemistry 29: 3959–3965; Good A H, Cooper D K C, Malcolm A J, Ippolito R M, Koren E, Neething F A, Ye Y, Zuhdi N and Lamontagne L R (1992) Transplantation Proceedings 24:559–562). The α-Gal epitope is universally present in the animal kingdom, with the exception of humans and Old World monkeys who lack the galactosyltransferase responsible for the epitope synthesis. Conversely, in normal human serum there are significant amounts of naturally occurring anti-αGal antibodies, which constitute approximately 1–3% of total IgG molecules and 3–5% of total IgM (Rother R P and Squinto S P (1996) Cell 86:185–188). Recent studies suggest that anti-αGal IgM, rather than IgG, is responsible for the hyperacute rejection response observed in organ xenotransplantation (Kroshus T J, Bolman R M III, and Dalmasso A P (1996) Transplantation 62:5–12).

The second immunological barrier to xenografts is termed delayed or vascular rejection. Although a detailed mechanism has yet to be elucidated, vascular endothelium cells are considered to be the target for immune activation through antibody-dependent cytotoxicity mediated by NK cells and macrophages (Lawson J H, and Platt J L (1996) Transplantation 63:303–310). In contrast to hyperacute rejection, both IgG and IgM induce vascular rejection effectively, and complement is apparently not involved. These antibodies may represent xenoreactive natural antibodies whose specificities have not yet been characterized. Finally, the cellular immune response constitutes the last barrier for xenotransplantation. The mechanism involved is probably similar to that observed in allograft rejection, but with more potent responses.

Figure 1:
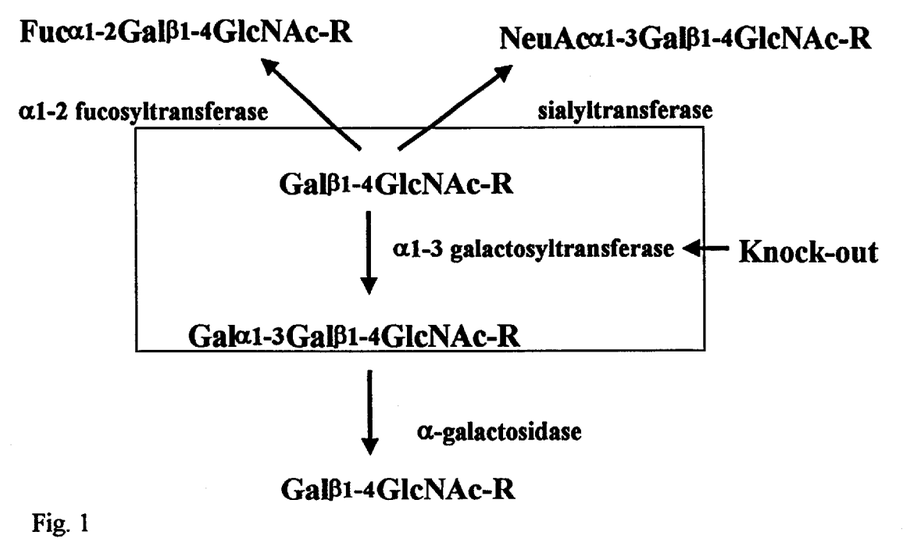

Although immune responses to xenografts are divided into three stages, most research and clinical strategies thus far developed have been aimed only at the first stage, hyperacute rejection. One approach to reducing hyperacute rejection involved circulating human recipient blood over an αGal immunoadsorbent column to remove anti-αGal antibodies prior to transplantation of the xenograft (Taniguchi S, Neethling F A, Korchagina E Y, Bovin N, Ye Y, Kobayashi T, Niekrasz M, Li S, Koren E, Oriol R, Cooper D K C (1996) Transplantation 62:1379–1384). However, while the procedure was successful in reducing the concentration of anti-αGal antibodies in the human blood, the reduction in antibody levels was transient, and was often followed by a rapid rebound within days. A more attractive alternative is to alter the αGal epitope on the donor organ by expressing or knocking out specific glycosyltransferase/glycosidase activities in organ donor animals (Osman N, McKenzie I F C, Ostenried K, Ioanou Y A, Desnick R J, and Sandrin M S (1997) Proc Natl Acad Sci 94:14677–14682; Koike C, Kannag, R, Takuma Y, Akutsu F, Hayashi S, Hiraiwa N, Kadomatsu K, Muramatsu T, Yamakawa H, Nagai T, Kobayashi S, Okada H, Nakashima I, Uchida K, Yokoyama I, and Takagi H (1996) Xenotransplantation 3:81–86) (see FIG. 1). A third approach is to generate transgenic animals that express human complement regulatory proteins, such as DAF, CD46 and CD59 (Zaidi A, Schmoeckel M, Bhatti F, Waterworth P, Tolan M, Cozzi E, Chavez G, Langford G, Thiru S, Wallwork J, White D, and Friend P (1998) Transplantation 65: 1584–1590). In this approach, although binding of xenoreactive antibodies still takes place, the presence of these regulatory proteins may prevent complement-induced cell lysis. Data from several studies seem to suggest that a combination of different approaches may be required to efficiently inhibit hyperacute rejection associated with xenograft transplantation.

In recent years, a consensus has emerged that the domestic pig may represent a good alternative to nonhuman primates as a donor of organs for transplantation. Porcine and human organs have similar sizes and cardiac output efficiencies. Pigs are relatively easy and inexpensive to raise in large numbers. Furthermore, pigs can be more easily raised in sterilized environments than nonhuman primates, and the use of pigs as organ donors produces fewer ethical concerns. The greater phylogenetic distance between pigs and humans means it is less likely that xenografts of pig organs or cells would impose any realistic risk of transmitting an infectious organism of epidemiological significance to the human population. However, the immunological and physiological incompatibility between pigs and humans remains a significant obstacle to the widespread use of pig organs for transplantation.

Advances in the field of xenotransplantation have brought to light the intriguing prospect of using porcine blood for use in xenotransfusions. Serologically, human blood and pig blood have a number of important features in common, including a similar hematocrit, blood volume, and number of blood groups. Biochemically, human hemoglobin has been expressed in pig and functions normally in vivo (Rao M J, Schneider K, Chait B T, Chao T L, Keller H, Anderson S, Manjula B N, Kumar R, and Acharya A S (1994) *Artif Cells Blood Substit Immobil Biotechnol* 22:695–700). However, surface antigens on porcine red blood cells ("pRBCs") are significantly different from those identified on human red blood cells, and are recognized by antibodies in human serum. Thus, pRBCs would certainly be short lived if injected into human blood circulation. Since donor endothelium is not involved, the reactions in human immunological responses to pRBCs are probably different from the reactions associated with organ transplantation. One may gain some insight into the human immune responses to pRBCs from a consideration of the fate of mismatched red cells upon allo-transfusion in humans. There are two principal mechanisms of in vivo red cell destruction in allo-transfusion (*Transfusion Reactions in Applied Blood Group Serology*, Chapter 36, 4$^{th}$ Edition (1998) (Eds. Issitt, P D and Anstee D J) Montgomery Scientific Publications, Durham, N.C.). The first mechanism, termed intravascular destruction, is triggered by antibody binding and complement activation. Red cells are thus rapidly lysed and release hemoglobin into the blood stream. IgG molecules may play a major role in intravascular destruction, since many IgM antibodies against blood groups are cold-reactive and do not bind efficiently to red cells in vivo. The second mechanism for clearing red cells in vivo is extravascular destruction, in which intact red cells are removed from circulation primarily by macrophages in the liver and spleen. In this case red cells are coated with IgG, but not at a high enough concentration to activate the complete complement cascade. Under these conditions, the complement cascade is usually halted at the C3 stage.

As is the case with other porcine cells thus far studied, pRBCs carry the αGal epitope on the cell surface, and this epitope accounts for the major reaction observed with xenoreactive human natural antibodies. However, there are data suggesting that porcine red cells may also carry additional xenoantigens other than the αGal epitope (MacLaren L, Lee T D G, Anderson D, Nass M, and McAlister V C (1998) *Transplant Proc* 30:2468). The natures of these non-αGal xenoantigens and corresponding human xenoreactive antibodies have not been explored. Identification of these non-αGal epitopes and finding ways to reduce or eliminate host immune rejection responses directed to these epitopes is important to fully realize the potential benefits of using porcine organs in xenotransplantation.

SUMMARY OF THE INVENTION

The present invention is directed to a porcine xenoantigen that does not include an αGal epitope. The present invention is also directed to agents which bind to the porcine xenoantigen.

The present invention also provides methods for the isolation of the porcine xenoantigen and for the isolation of human xenoreactive antibodies that bind to the antigen, as well as kits useful in practicing these methods.

The present invention further provides methods and pharmaceutical compositions for treating a host rejection response to a xenograft which employ the isolated porcine xenoantigen, or the agents that bind to the antigen.

The present invention still further provides a method for treating a porcine xenograft that renders it suitable for transplantation into a subject in need of such a xenograft. The method includes treating the xenograft with the porcine xenoantigen or, alternatively, an agent which binds the porcine xenoantigen.

A method for removing human antibodies that react with the porcine xenoantigen is also provided by the present invention.

Additional objects of the invention will be apparent from the description which follows.

BRIEF DESCRIPTION OF THE FIGURES

FIG. 1 represents possible transgenic approaches to eliminating the αGal epitope in animals. The αGal epitope (Galα1,3Galβ1,4GlcNAc), synthesized by α1,3 galactosyltransferase, is the major antigen responsible for hyperacute rejection responses. Strategies that are being tested to block the αGal epitope include, but are not limited to, the in vivo expression of α1,2 fucosyltransferase, sialyltransferase and α-galactosidase, and the production of α1,3 galactosyltransferase knockout animals.

FIGS. 3A and 3B represent the procedure for measuring human complement-mediated hemolysis. The procedure is outlined in FIG. 3B. Hemolysis (FIG. 3A) is plotted as percent lysis versus volume of human serum added ($\mu l$). Lysis is defined as $(OD-OD_o)/(OD_{100}-OD_o)$, where OD represents the amount of lysis, as measured by the absorbance at 541 nm, $OD_o$ is the absorbance at 541 nm that is due to spontaneous lysis in the absence of any additions, and $OD_{100}$ is the absorbance at 541 nm that is due to 100% lysis of red cells under the experimental conditions.

FIG. 7 represents the effect of the trisaccharide of FIG. 4 on the binding of fractions S1 and S2 to pRBCs. 40 µl of the trisaccharide (2 mg/ml) was added to 2 µl of S1 or S2 plus 38 µl of PBS (final concentration of trisaccharide 1 mg/ml), followed by incubation at 4° C. overnight. pRBCs were then added and flow cytometry analysis performed, using anti-human IgG (H+L) conjugated with phycoerythrin (PE) as the secondary antibody. Sample 1: negative control lacking the primary and secondary antibodies. Sample 2: negative control containing the secondary antibody only. Samples 3 and 4: fraction S1 without and with the trisaccharide of FIG. 4, respectively. Samples 5 and 6: fraction S2 without and with the trisaccharide of FIG. 4, respectively.

FIG. 8 represents the effect of concentration of the trisaccharide of FIG. 4 on the binding of S1 to pRBCs. Fraction S1 was incubated with various amounts of the trisaccharide under the same conditions described in FIG. 4. The binding of IgG (curve 1) and IgM (curve 2) molecules from fraction S1 was monitored by flow cytometry, using anti-human IgG and anti-human IgM, respectively. The data from the flow cytometry analyses were plotted as mean fluorescent intensity (MFI) versus the final concentration of trisaccharide, and the curves were generated by nonlinear curve fitting.

(FIG. 9A) anti-αGal antibody incubated in the absence (curve 3) or presence (curve 4) of the trisaccharide (1 mg/ml). (FIG.9B): Non-αGal antibodies incubated in the absence (curve 3) or presence (curve 4) of the trisaccharide (1 mg/ml).

(FIG. 10A): pRBC-bound IgG (2) and IgM (3) molecules incubated with fraction S2. (FIG. 10B): pRBC-bound IgG (4) and IgM (5) incubated with non-anti-αGal antibodies. Curve 1: negative control lacking the primary and secondary antibodies.

(FIG. 13A) anti-human IgM used as the secondary antibody. (FIG. 13B) anti-human IgG used as the secondary antibody. Curve 1: negative control lacking the primary and secondary antibodies.

(FIG. 14A) Samples from different steps of purification were separated by SDS-PAGE, and visualized by silver staining. Lane 1: red cell membranes (3 µl). Lane 2: unbound fraction from the anti-human IgG and anti-human IgM columns (10 µl). Lane 3: samples loaded onto the anti-human IgG column (10 µl). Lane 4: eluate from the anti-IgM column (15 µl). Lane 5: eluate from the anti-IgG column (15 µl). (M): Molecular weight standards expressed in kDa. (FIG. 14B) Concentrated eluate from the anti-human IgG column was separated by SDS-PAGE (1), then transferred to a PVDF membrane and visualized by Coomassie blue staining. Protein bands marked H and L corresponded to immunoglobulin heavy and light chains, respectively. The 45 kDa band (arrow) was excised for direct N-terminal sequencing. (M): Pre-stained protein molecular weight markers, expressed in kDa.

DETAILED DESCRIPTION OF THE INVENTION

The present invention provides a purified porcine xenoantigen, found on porcine red blood cells, which binds to a xenoreactive human antibody and which does not include an αGal epitope. As used herein, a xenoantigen is an antigen which is found in or on cells of a nonhuman animal and which is not found in or on human cells. A xenoreactive human antibody refers to a human antibody that binds specifically to a xenoantigen. The purified antigen is preferably a protein, and further preferably is a protein having a molecular weight of about 45 kDa, as measured by SDS polyacrylamide gel electrophoresis. The purified antigen is also preferably a protein comprising the amino acid sequence Asp-Val-Xaa-Pro-Val-Glu-Ser-Val-Xaa (SEQ ID NO:1), wherein Xaa refers to any of the twenty amino acids which occur naturally in mammals. The amino acid sequence of SEQ ID NO:1 may be an amino-terminal sequence. The antigen may also be a polysaccharide or a lipid, or any combination of a protein, a polysaccharide, or a lipid, so long as the antigen does not include an αGal epitope. The antigen of the present invention may be isolated from porcine red blood cells or recombinantly produced. It is also within the confines of the present invention that the antigen includes similar or identical antigens from other porcine tissues which bind to a xenoreactive human antibody and which do not include an αGal epitope.

The present invention also provides a purified agent which binds to a purified porcine xenoantigen. The antigen is any that does not include an αGal epitope. More specifically, the porcine xenoantigen is found on porcine red blood cells. Preferably, the agent is any molecule that specifically binds to a purified porcine xenoantigen and inactivates or blocks the binding of the antigen to a xenoreactive human antibody. The agent may be in the form of an antibody, an Fab fragment, an F(ab')$_2$ fragment, an Fv antibody, a drug, a peptide, a protein, a nucleic acid, a lipid, a polysaccharide, or any combination thereof. An Fab fragment is a univalent antigen-binding fragment of an antibody which is produced by papain digestion. An F(ab')$_2$ fragment is a divalent antigen-binding fragment of an antibody which is produced by pepsin digestion. An Fv antibody is a hybrid antibody molecule usually produced by phage display methods. Antibodies useful in the present invention may be either monoclonal antibodies or polyclonal antibodies. Antibodies may be produced by any of a number of methods well-known to those in the art. Drugs include small organic or inorganic molecules. Where the agent is a polysaccharide, any polysaccharide can be used that is effective to bind to a purified porcine xenoantigen and block the binding of the antigen to a xenoreactive human antibody, so long as the polysaccharide does not contain an αGal epitope.

The present invention also provides a method for the isolation of non-αGal porcine xenoantigens from porcine tissues or cells. The method comprises the following steps: (a) contacting human sera with an α-Gal epitope-containing molecule, whereby an antibody in the human sera binds to the α-Gal epitope-containing molecule to form a complex; (b) removing the complex from the human sera to produce an anti-αGal antibody-depleted sera; (c) contacting the anti-αGal antibody-depleted sera with porcine tissue or cells, whereby at least one human xenoreactive antibody present in the anti-αGal antibody-depleted sera binds to an antigen present on the porcine tissue or cells; (d) isolating the tissue or cells bound to the xenoreactive antibody; (e) separating the human xenoreactive antibody bound to the antigen from the tissue or cells; and (f) eluting the antigen from the human xenoreactive antibody.

The αGal epitope-containing molecule of the method described above preferably includes the trisaccharide Galα1,3Galβ1,4GlcNAc, and is further preferably attached to a solid support, such as an insoluble organic polymer in the form of a bead, gel or plate. Examples of suitable solid supports include, without limitation, dextran, agarose, cellulose, polystyrene, polyacrylamide, or other insoluble organic polymers. The trisaccharide attached to the solid support may be used as a slurry, or in the form of a column, cartridge, or plate. The αGal epitope may further be attached to the solid support through a spacer molecule if desired.

The αGal epitope-containing molecule binds to an anti-αGal antibody in the serum to produce a complex, e.g., an antigen/antibody complex, and an anti-αGal antibody-depleted serum. After binding, the complex may be separated from the serum by methods well known to those in the art. For example, if the trisaccharide attached to the solid support is in the form of a column or a cartridge, the serum may be passed through the column or cartridge and the resulting serum extract treated as the anti-αGal antibody-depleted serum. If the trisaccharide is attached to the solid support in the form of a plate, or is attached directly to a plate, the serum may be passed over the surface of the plate by panning and then removed and thereafter treated as the anti-αGal antibody-depleted serum. If the trisaccharide attached to the solid support is in the form of a slurry, the complex may be separated from the serum by filtration, or by sedimenting or centrifuging the slurry, followed by decanting to separate the liquid phase from the solid-containing phase. If the trisaccharide is not bound to a solid support, the binding may also be performed under conditions whereby the complex is rendered insoluble upon formation. Thereafter, the complex may be removed from the serum by any appropriate method, including but not limited to sedimentation, centrifugation or filtration.

After the αGal-antibody depleted serum is obtained, it is contacted with porcine tissue or cells. The porcine tissue or cells may be any tissue or cells that bears a non-αGal epitope xenoantigen. Suitable tissues or cells may include endothelial cells, liver, heart, brain, kidney, intestine, pancreas, lung, skin, bone marrow, blood, red blood cells, and the like, and preferably porcine red blood cells or porcine red blood cell membranes, or any derivatives thereof. The tissue or cells are contacted with the αGal-antibody depleted serum under conditions that promote binding of the antigen to a non-anti-αGal human xenoreactive antibody in the αGal-antibody depleted serum. These appropriate bind conditions (e.g. temperature, pH and salt concentration) are readily determinable by the skilled artisan. After contacting the tissue or cells with the αGal-antibody depleted serum for a period of time sufficient to bind the antibody, the tissue or cells is thereafter separated from the serum by any appropriate means. These means may include, but are not limited to, sedimentation, centrifugation, or filtration. Alternatively, the tissue or cells may be bound to a solid support in the form of a column, cartridge or plate, and the serum separated from the tissue or cells by passage through the column or cartridge or by panning over the plate.

Thereafter, the tissue or cells are contacted with a purified antibody that binds selectively to the non-anti-αGal human xenoreactive antibody bound to the antigen on the tissue. The purified antibody may be an anti-human IgG antibody, an anti-human IgM antibody, or a combination of these. These antibodies are widely available through commercial suppliers and are well known to those in the art. Again, the purified antibody is contacted with the tissue or cells under conditions (temperature, pH, and salt concentration) that promote binding of the purified antibody to the human xenoreactive antibody bound to the antigen on the tissue or cells. Thereafter, the tissue or cells are separated from the purified antibody, which is bound to the human xenoreactive antibody, which in turn is bound to the antigen. The separation is performed under conditions that permit the ternary complex of purified antibody-xenoreactive antibody-antigen to remain intact, yet be separated from the remainder of the tissue or cells and other components of the mixture. This may require treatment of the tissue or cells in any of a number of ways, such as, without limitation, physical or enzymatic dissociation of the tissue or solubilization by detergents. This separation is possible in view of the strong interaction between antibodies and their antigens. However, any procedures used to separate the antigen from the tissue or cells preferably does not also result in the dissociation of the components of the ternary complex.

Thereafter, the antigen is eluted from the ternary complex by any appropriate method. Examples include heat elution (i.e., 57° C. for 5 min) or elution using acid or base. The eluted antigen may thereafter be further purified, if required, by appropriate methods well known to those in the art.

The present invention also provides a method for isolating a human xenoreactive antibody which binds to a porcine xenoantigen that does not include an αGal epitope. The method comprises the steps of: (a) contacting human sera with an α-Gal epitope-containing molecule, whereby an antibody in the human sera binds to the α-Gal epitope-containing molecule to form a complex; (b) removing the complex from the human sera to produce an anti-αGal antibody-depleted sera; (c) contacting the anti-αGal antibody-depleted sera with porcine tissue or cells, whereby at least one human xenoreactive antibody present in the anti-αGal antibody-depleted sera binds to an antigen present on the porcine tissue or cells; (d) isolating the tissue or cells bound to the xenoreactive antibody; (e) separating the human xenoreactive antibody bound to the antigen from the tissue or cells; and (f) eluting the human xenoreactive antibody from the antigen.

It will be appreciated that the method for isolation of the agent outlined above is very similar to that previously discussed for isolating the antigen, with the exception of the final step (step (f)). The steps for eluting the human xenoreactive antibody from the purified antibody implicate the same concerns as for the elution of the antigen. Therefore, the human xenoreactive antibody may be purified from the anti-human antibody and the porcine antigen by any appropriate means, as outlined above for the antigen.

The present invention also provides a method for detecting the presence of a porcine red blood cell antigen in a sample. The method may be performed by contacting a sample with an agent which binds to a porcine antigen under conditions permitting the antigen, if present in the sample, to bind to the agent to form a complex, and thereafter detecting the presence of the complex. The antigen is one that does not include an αGal epitope. The agent may be any of an antibody, an Fab fragment, an F(ab')$_2$ fragment, an Fv antibody, a drug, a peptide, a protein, a nucleic acid, a lipid, a polysaccharide, or any combination thereof. The agent is preferably an antibody, and more preferably a monoclonal antibody, directed against the antigen. Where the agent is an antibody, an Fab fragment, an F(ab')$_2$ fragment, or an Fv antibody, the method may be performed as an ELISA assay, a Western blot, or as any other immunostaining method employing an antigen-antibody interaction. The present invention also contemplates the provision of a kit for performing the method of detecting the presence of a porcine antigen in a sample, as described above. The kit would include a container, an agent which binds to a porcine antigen to form a complex, and a reagent or reagents capable of detecting the resulting complex. As noted above, the antigen is one that binds to a human xenoreactive human antibody, and which does not include an αGal epitope. The reagent or reagents capable of detecting the complex are preferably secondary antibodies that bind selectively to one or the other of the antigen and the agent, preferably the agent, and which are further linked, either through a covalent linkage or by a noncovalent linkage, to a reporter molecule, including but not limited to an enzyme, a fluorescent molecule, a radioactive molecule, or a light-emitting molecule.

The present invention also provides a method for detecting the presence, in a sample, of a xenoreactive human antibody that binds to a porcine antigen. The method may be performed by contacting a sample with a porcine antigen that binds to a xenoreactive human antibody to form an antigen-antibody complex, and thereafter detecting the presence of the antigen-antibody complex. The porcine antigen is one that does not include an αGal epitope. The method may be performed as an ELISA assay, a Western blot, or as any other immunostaining method employing an antigen-antibody interaction. The present invention also contemplates the provision of a kit for performing the method of detecting the presence of a xenoreactive human antibody that binds to a porcine antigen in a sample, as described above. The kit would include a container, a porcine antigen, and a reagent or reagents capable of detecting the resulting antigen-antibody complex. As noted above, the porcine antigen is one that binds to a human xenoreactive human antibody, and which does not include an αGal epitope. The reagent or reagents capable of detecting the complex are preferably secondary antibodies that bind selectively to one or the other of the antigen and the agent, preferably the agent, and which are further linked, either through a covalent linkage or by a noncovalent linkage, to a reporter molecule, including but not limited to an enzyme, a fluorescent molecule, a radioactive molecule, a light-emitting molecule, and other known reporter molecules.

The present invention also provides a method of treating a host rejection response to a xenograft in a subject in need of such treatment which comprises administering either a purified antigen that binds to a human xenoreactive antibody, or an agent which binds to the purified agent that binds to a human xenoreactive antibody. In either case, the antigen or agent is administered in an amount which is effective to reduce the host rejection response in the subject. That is, the amount administered is an amount effective to reduce one or more of the hyperacute rejection, the delayed or vascular rejection, and the cellular immune response associated with xenotransplantation. This amount is readily determinable by one skilled in the art, and may vary among patients. Administration may be by any appropriate method, including but not limited to oral, sublingual, parenteral, or transdermal administration, or administration by suppository, and preferably parenteral administration.

Furthermore, a pharmaceutical composition for treating a host rejection response to a xenograft comprises either a purified antigen that binds to a human xenoreactive antibody, or an agent which binds to the purified agent that binds to a human xenoreactive antibody. In either case, the antigen or agent is provided in an amount which is effective to reduce the host rejection response in the subject. The pharmaceutical composition further comprises a pharmaceutically acceptable carrier. The pharmaceutically acceptable carrier must be "acceptable" in the sense of being compatible with the other ingredients of the formulation and not deleterious to the recipient thereof. Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, and water, among others. The formulations may conveniently be presented in unit dosage and may be prepared by methods well-known in the pharmaceutical art, by bringing the active compound into association with a carrier or diluent, as a suspension or solution, and optionally adding one or more accessory ingredients, e.g. buffers, flavoring agents, surface active agents, and the like. The choice of carrier will depend upon the route of administration.

For oral and sublingual administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; and with lubricants such as talc or magnesium stearate.

For parenteral administration, the antigen or agent may combined with a sterile aqueous solution which is preferably isotonic with the blood of the recipient. Such formulations may be prepared by dissolving a solid active ingredient in water containing physiologically compatible substances such as sodium chloride, glycine, and the like, and having a buffered pH compatible with physiological conditions to produce an aqueous solution, and rendering the solution sterile. The formulations may be present in unit or multi-dose containers such as sealed ampoules or vials.

For transdermal administration, the antigen or agent may be combined with skin penetration enhancers such as propylene glycol, polyethylene glycol, isopropanol, ethanol, oleic acid, N-methylpyrrolidone, and the like, which increase the permeability of the skin to the compounds, and permit the compounds to penetrate through the skin and into the bloodstream. The antigen or agent also may be combined additionally with a polymeric substance such as ethylcellulose, hydroxypropyl cellulose, ethylene/vinylacetate, polyvinyl pyrrolidone, and the like, to provide the composition in gel form, which can be dissolved in a solvent such as methylene chloride, evaporated to the desired viscosity, and then applied to backing material to provide a patch.

For administration by suppository, the antigen or agent may be combined with any appropriate base to form a mass that is solid at room temperature but dissolves at body temperature. The base may include, without limitation, cocoa butter, glycerinated gelatin, hydrogenated vegetable oils, polyethylene glycols of various molecular weights, fatty acid esters of polyethylene glycols, and the like.

The present invention also provides a method of treating a porcine xenograft to render the xenograft suitable for transplantation, comprising the step of contacting the xenograft with an agent that binds a porcine xenoantigen in an amount effective to reduce a host rejection response in a subject receiving the xenograft. The porcine xenoantigen is one that does not include an αGal epitope. The present invention also provides a xenograft that has been treated according to the method outlined above. The xenograft may include, without limitation, blood, a blood product, a red blood cell composition, endothelial cells, bone marrow, a liver, a kidney, a lung, or a heart, or any combination thereof. The amount of the agent administered is an amount effective to reduce the host rejection response in the subject, by blocking the interaction of the porcine xenoantigen on the xenograft with human xenoreactive antibodies. The amount administered is further an amount effective to reduce one or more of the hyperacute rejection, the delayed or vascular rejection, and the cellular immune response associated with xenotransplantation. This amount is readily determinable by one skilled in the art, and may vary among patients.

The present invention also provides a method of removing human xenoreactive antibodies from blood or a blood-derived composition, comprising the steps of contacting the blood or blood-derived composition with an antigen which binds to a human xenoreactive antibody to form an antigen-antibody complex, and removing the resulting antigen-antibody complex from the blood or blood-derived composition. The present invention also provides a blood or blood-derived composition that has been treated by the above-described method. As noted above, the antigen does not include an αGal epitope. The antigen may be attached to a solid support, such as an insoluble organic polymer in the form of a bead, gel or plate. Examples include, without limitation, dextran, agarose, cellulose, polystyrene, polyacrylamide, or other insoluble organic polymers. The antigen attached to the solid support may be used as a slurry, or in the form of a column, cartridge or plate. The antigen may further be attached to the solid support through a spacer molecule if desired.

The antigen binds to xenoreactive antibodies in the blood or blood-derived composition to produce a complex, e.g., an antigen/antibody complex. After binding, the complex may be removed from the blood or blood-derived composition by methods well known to those in the art. For example, if the antigen attached to the solid support is in the form of a column or a cartridge, the blood or blood-derived composition may be passed through the column or cartridge. If the antigen is attached to a solid support in the form of a plate, or attached directly to a plate, the blood or blood-derived composition may be passed over the surface of the plate by panning and then removed. If the antigen attached to the solid support is in the form of a slurry, the complex may be separated from the blood or blood-derived composition by filtration, or by sedimenting or centrifuging the slurry, followed by decanting to separate the liquid phase from the solid-containing phase.

The present invention is further described in the following Experimental Details section which is set forth to aid in the understanding of the invention, and should not be construed to limit in any way the scope of the invention as defined in the claims which follow thereafter.

Experimental Details 1. pRBC Agglutination with Human Serum and Antibodies Against Human Blood Group Antigens At least 16 blood groups on pRBCs have been serologically identified (Erythrocyte antigens: the immune responses to red cells as an example of type II reactions in *An Introduction to Veterinary Immunology* (1982) pp. 276–283). Chromosome loci for 14 of these blood groups have been determined. However, their biochemical properties have not yet been well characterized. Even less is known in terms of their correlation with blood group antigens identified on human red blood cells. Toward that end, we carried out agglutination test using pRBCs and antibodies against various human blood group antigens. As shown in Table 1, pRBCs may carry type A or type B antigen or neither. The type A carbohydrate chain has been previously isolated from pRBCs and is recognized by either polyclonal or monoclonal anti-A in our studies. On the other hand, monoclonal anti-B antibody selectively agglutinates type B pRBCs whereas polyclonal anti-B reacts with all the samples tested. The simplest explanation is that the polyclonal, but not the monoclonal, antibody may contain a subset that interacts with the ubiquitous αGal epitope (linear type B structure). Furthermore, although the αGal epitope is present in all porcine blood samples its level of expression on the cell surface varies significantly (MacLaren L, Lee T D G, Anderson D, Nass M, and McAlister V C (1998) *Transplant Proc* 30:2468).

TABLE 1

| Antibody | Strength | Antibody | Strength |
| --- | --- | --- | --- |
| polyclonal anti-A | 4 +/− | anti-Fy | 0 |
| monoclonal anti-A | 2 +/− | anti-P | 0 |
| polyclonal anti-B | 4 + | anti-$P_1$ | 0 |
| monoclonal anti-B | 1 +/− | anti-M | 0 |
| anti-A,B | 4 + | anti-N | 0 |
| monoclonal anti-H | 0 | anti-K | 0 |
| monoclonal anti-D | 0 | anti-k | 0 |
| anti-C | 0 | anti-S | 0 |
| anti-c | 0 | anti-s | 0 |
| anti-E | 0 | anti-I | 3 + |
| anti-e | 0 | anti-Le$^b$ | 0 |

Figure 2:
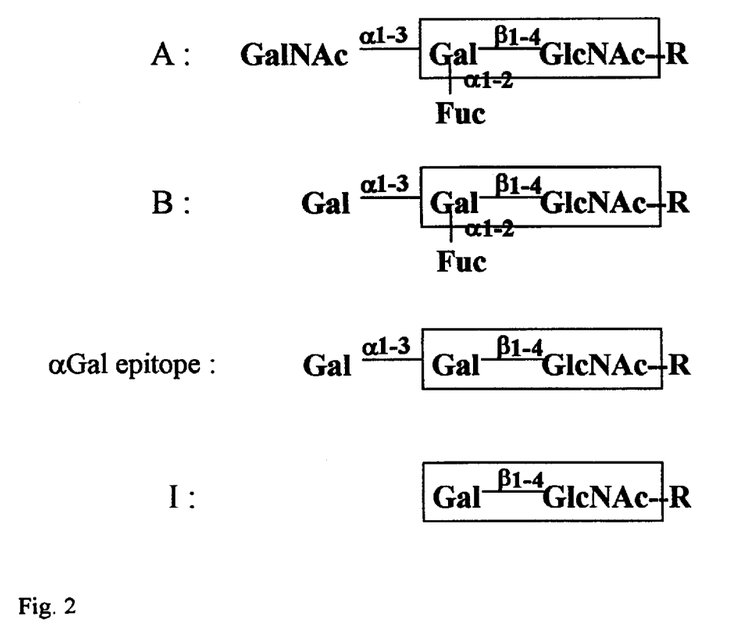
FIG. 2 represents the chemical structure of the αGal epitope and related oligosaccharide structures.

The only other anti-human blood group antibody that reacts with pRBCs is anti-I. Of all the samples tested, the agglutination strength for anti-I is consistently between 2+ to 3+, suggesting that the I antigen (Galβ1,4GlcNAc) may exist on all red cells regardless of their other blood groups (e.g. type A or B). Thus, structurally, the I antigen may be considered a precursor for the type A, B and the αGal epitopes (FIG. 2).

It is not surprising that none of the antibodies against human protein antigens reacted with pRBCs in hemagglutination assays. Due to their phylogenetic distance, human protein antigens are most likely to be quite different in terms of antigenicity from their counterparts in pRBCs, if such counterparts exist at all. Rh and Duffy protein are two major protein antigens on human red cells, but polyclonal antibodies against these two proteins failed to crossreact with their counterparts in mouse (Apoil P, and Blancher A (1999) *Immunogenetics* 49:15–25; Luo H, Chaudhuri A, Johnson K R, Neote K, Zbrzezna V, He Y, and Pogo A O (1997) *Genome Res* 7(9):932–41). It is thus very interesting to determine whether any protein antigens on porcine red blood cells are involved in the binding of xenoreactive natural antibodies in human serum.

When normal human serum from type AB individuals was used in a hemagglutination assay with pRBCs, we observed agglutination strengths of between 2+ and 3+ with 1 μl of serum in 120 μl reaction. Since the type AB serum contains neither anti-A nor anti-B antibodies, reactions involving type A or B antigens on pRBCs can thus be excluded. It has been reported that anti-αGal is the major xenoreactive antibody in human serum and is largely responsible for hemagglutination in vitro. We prepared an anti-αGal depleted antibody fraction by using a specific ligand affinity column, as described below. This fraction produced an agglutination strength of 2+ in the hemagglutination test with pRBCs and was not affected by pre-incubation with trisaccharide Galα1,3Galβ1,4GlcNAc at a concentration of 1 mg/ml. This is the first indication that pRBCs are recognized by xenoreactive antibodies other than anti-αGal in human serum.

2. Human Complement-Mediated pRBC Hemolysis

In blood transfusions between humans, mismatched red cells undergo intravascular destruction by the same mechanism as complement-induced hemolysis observed in vitro. To shed light on how the binding of human xenoreactive antibodies to pRBCs triggers the complement cascade and leads to hemolysis, we carried out in vitro complement-induced hemolysis reactions. Human serum containing all complement components was purchased from Sigma. Since this serum was derived from type B individuals, as determined by hemagglutination assays, we used only non-type A pRBCs in the complement assays to exclude the binding of anti-A antibody present in the serum.

Figure 3:
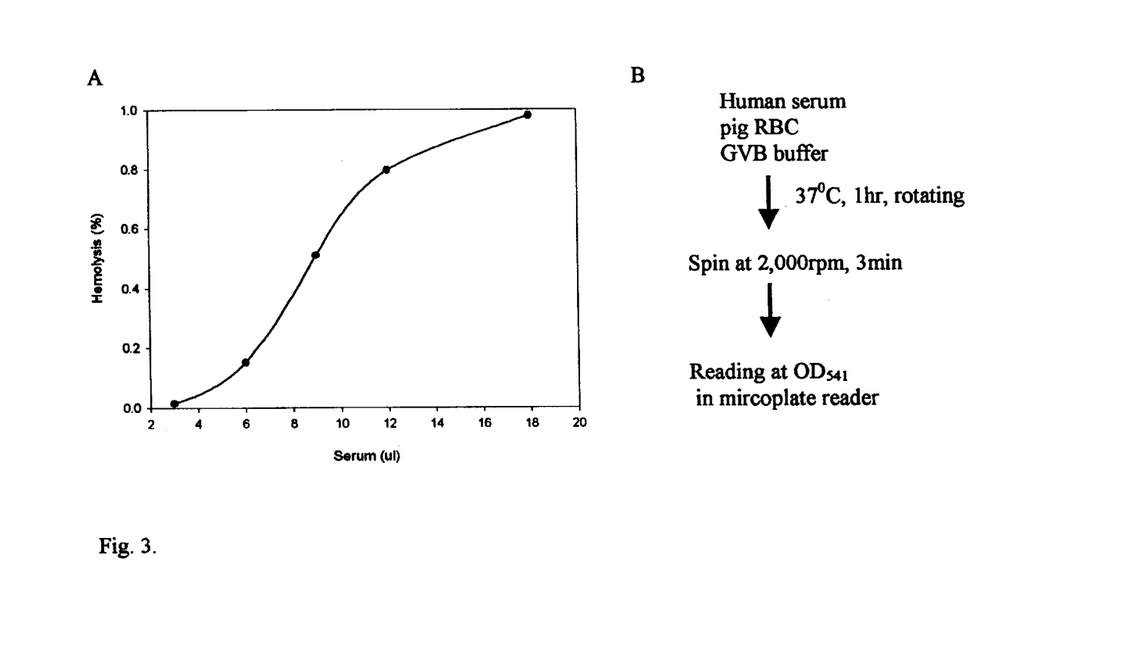

The human serum (between 3–18 μl) was mixed with 40 μl of 5% pRBCs (about $2 \times 10^7$ cells) in a total volume of 210 μl. After incubating at 370° C. for 1 hr with constant rotation, the remaining intact cells were removed from the reaction by centrifugation. Hemoglobin molecules released from the lysed cells into the supernatant were quantitated by measuring the absorbance at 541 nm. As shown in FIG. 3, a plot of pRBC lysis (%) versus the volume of serum added (μl) resulted in a typical S-shaped curve with $L_{50}=9$ ($L_{50}$ is defined as the amount of serum required to induce 50% of hemolysis). Our data indicate that the binding of xenoreactive natural antibodies in human serum to pRBCs triggers human complement-mediated hemolysis in vitro.

Figure 4:
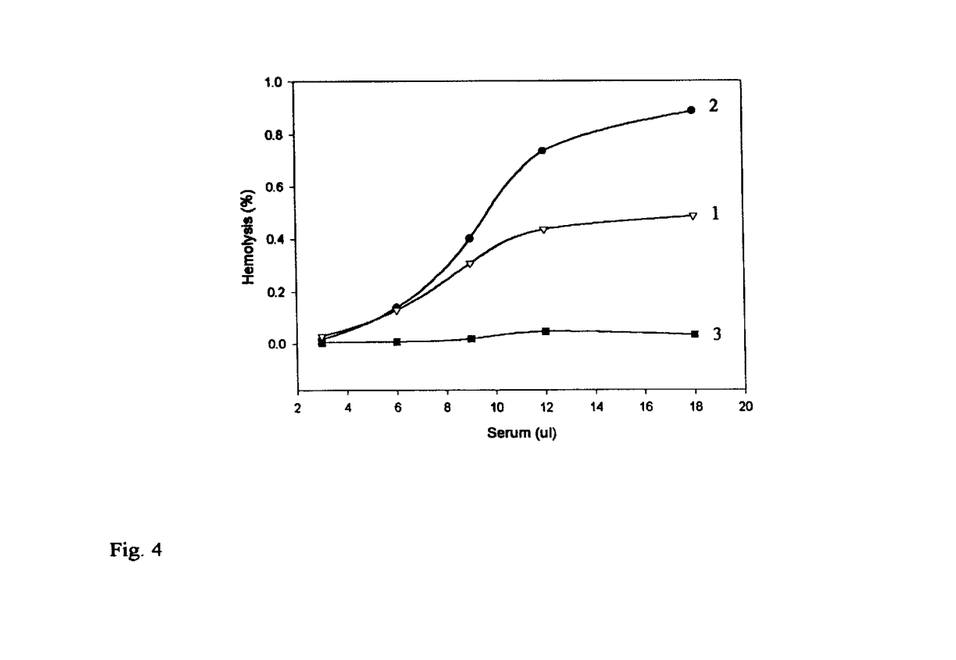
FIG. 4 shows a graph depicting the effect of the αGal epitope trisaccharide on complement-mediated hemolysis. Curve 1: human serum pre-incubated with the trisaccharide, Galα1,3Galβ1,4GlcNAc, at 4° C. for 1 hr, followed by a hemolysis assay as described in FIG. 3, panel B. Curve 2: hemolysis induced by serum alone without the inhibitor. Curve 3: hemolysis induced by heated-inactivated serum as a negative control.

In order to assess the contribution of anti-αGal and non-anti-αGal antibodies to the observed lysis, we incubated the human serum with pRBCs in the presence of the αGal epitope trisaccharide (final concentration 1 mg/ml) at 4° C. for 1 hr prior to the complement assay. Anti-αGal antibody in normal human serum can be completely inhibited by the trisaccharide at a concentration of 1 mg/ml, as determined by flow cytometry analysis (see below). As shown in FIG. 4, addition of the trisaccharide inhibitor significantly reduced the pRBC lysis. Compared to the control (without inhibitor), 1 mg/ml of trisaccharide blocked approximately 60% of hemolysis, suggesting that the remaining 40% of lysis may result from the binding of non-anti-αGal xenoantibodies present in human serum. As a negative control, human serum that was pre-incubated at 57° C. for 15 min lost complement activity and caused essentially no hemolysis, as shown in FIG. 4. The heat inactivation step did not affect the binding of xenoreactive antibodies to pRBCs, as determined by flow cytometry analysis (data not shown).

Figure 5:
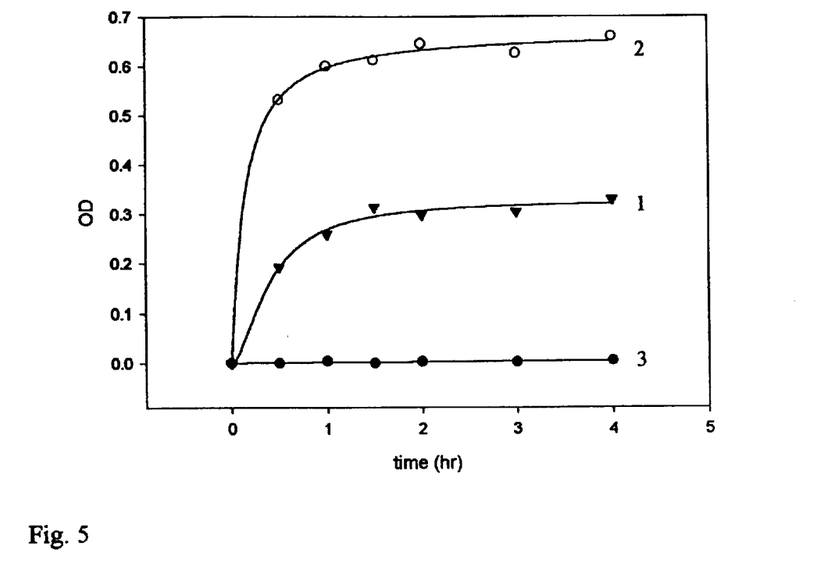
FIG. 5 shows the time-course for complement-induced hemolysis in the presence or absence of the trisaccharide of FIG. 4. The hemolysis was monitored up to 4 hr. The data were treated by regression curve fitting (Sigmoid Hill equation).

We also measured the time course for complement-mediated hemolysis of pRBCs (FIG. 5). Cell lysis proceeded rapidly in the first hour of incubation at 37° C., and then reached a plateau. This was true both in the presence and absence of 1 mg/ml trisaccharide. In this experiment, we observed approximately 50% inhibition of cell lysis by the trisaccharide. Another approach to elucidating the role of non-anti-αGal xenoantibodies in hemolysis is to reconstitute antibody-triggered, complement-mediated lysis by adding a non-anti-αGal antibody fraction to antibody-depleted human serum. Antibody-depleted human serum was prepared by passage over a protein A-resin column. However, numerous attempts failed to generate an antibody-depleted serum with full complement activity. This is presumably due to the loss of some complement elements during the antibody absorption by the protein A-conjugated resin.

3. Fractionation of Xenoreactive Human Natural Antibodies

Figure 6:
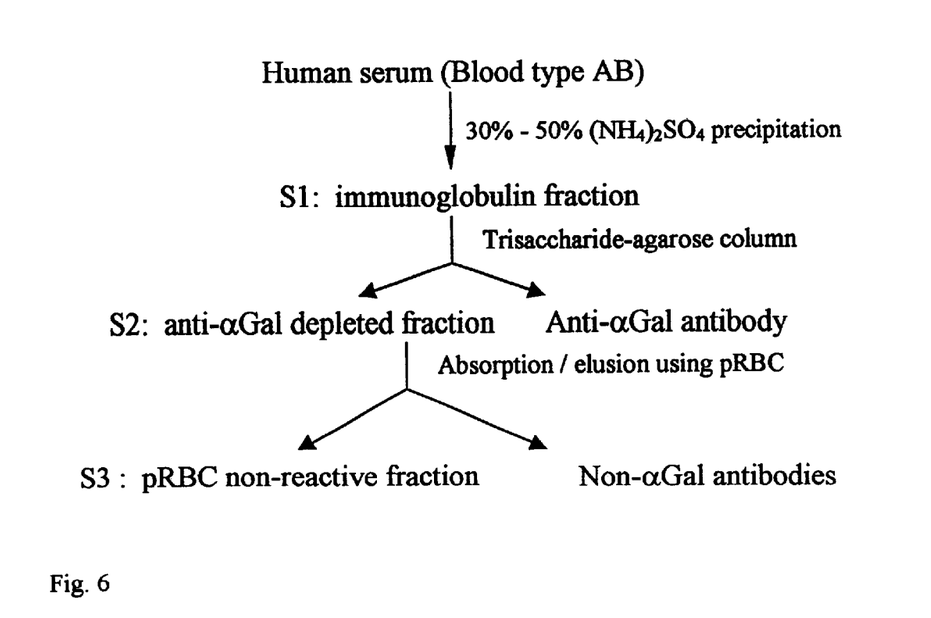
FIG. 6 represents a flow diagram showing the fractionation procedure of non-anti-αGal xenoreactive human antibodies from pooled blood type AB serum.

Pooled human sera from blood type AB individuals were used as the starting material for xenoreactive antibody fractionation (FIG. 6). After incubation at 56° C. for 15 min to inactivate complement, the human serum was subjected to ammonium sulfate precipitation. Proteins precipitated between 30% to 50% of $(NH_4)_2SO_4$ saturation were predominantly immunoglobulin and designated as fraction S1.

In order to separate anti-αGal antibodies from the S1 fraction, we prepared an affinity column using the trisaccharide as a ligand. A resin was constructed, using biotinylated poly[N-(2-hydroxyethyl)-acrylamide]Galα1,3Galβ1, 4GlcNAc (Syntesome, Munich, Germany) and streptavidin-agarose (Pierce, Rockford, Ill., USA). The resulting affinity resin had a capacity of approximately 0.1 nmole of trisaccharide per ml of resin. Based on reported levels of anti-αGal antibodies in normal human serum (1–3% of total IgG and 3–5% of total IgM), we added the S1 fraction to the affinity resin at a ratio of less than 50 ml of serum per ml of the resin to avoid saturating the column. After mixing for 3 hr at room temperature, the unbound fraction was separated and designated as fraction S2. The antibody bound resin was then washed extensively with phosphate buffered saline (PBS). The anti-αGal antibody was finally dissociated from the resin by incubating at 57° C. for 5 min.

To further isolate antibodies that recognize xenoantigens other than the αGal epitope, we used pRBCs as a specific immunoadsorbent. After incubating the S2 fraction with pRBCs for 1 hr at room temperature, the unbound fraction was collected by centrifugation and designated as the pRBC non-reactive fraction (S3). The bound antibodies (non-αGal antibodies) was then recovered from the pRBCs, using either a cold-acid method or a heat elusion method.

4. Characterization of Xenoreactive Antibodies by Flow Cytometry Analysis

Figure 7:
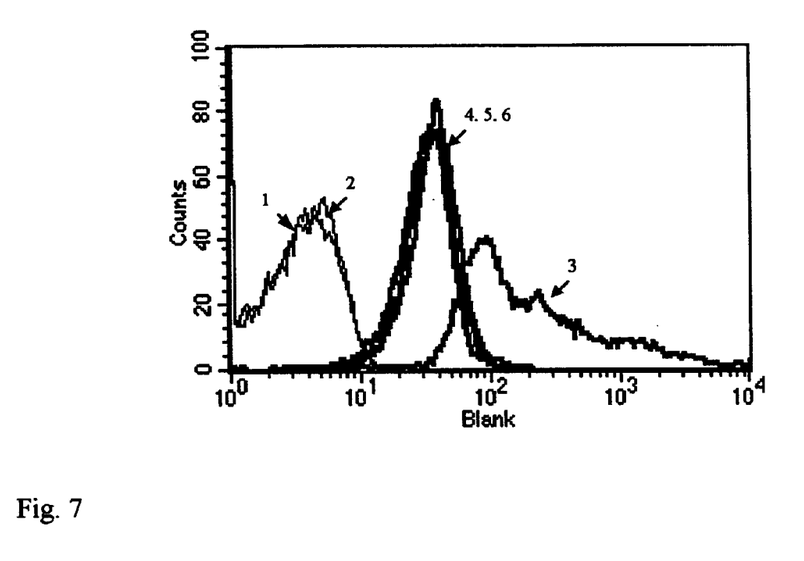

Various fractions derived from human serum were analyzed by flow cytometry. We first examined the binding of S1 and S2 to pRBCs in the presence or absence of the trisaccharide inhibitor Galα1,3Galβ1,4GlcNAc. As shown in FIG. 7, the binding of S1 is substantially inhibited by 1 mg/ml (1.7 mM) of the trisaccharide, resulting in a drop in MFI from 322 (sample 3) to 45 (sample 4). On the other hand, the binding of S2 to pRBCs was not significantly affected by the trisaccharide (sample 5 and 6). This suggests that the procedure used for the fractionation of human serum effectively generated an anti-αGal-depleted fraction (S2) without contaminating anti-αGal activity. Furthermore, the results indicate that human xenoreactive antibodies other than the well-characterized anti-αGal antibody recognize pRBCs. In addition, since we used the same volume (2 μl) of S1 and S2 in the assay, the fact that samples 4, 5 and 6 fell into approximately the same position on the histograph suggests that the inhibition by free trisaccharide achieved the identical effect as depletion by immobilized trisaccharide.

Figure 8:
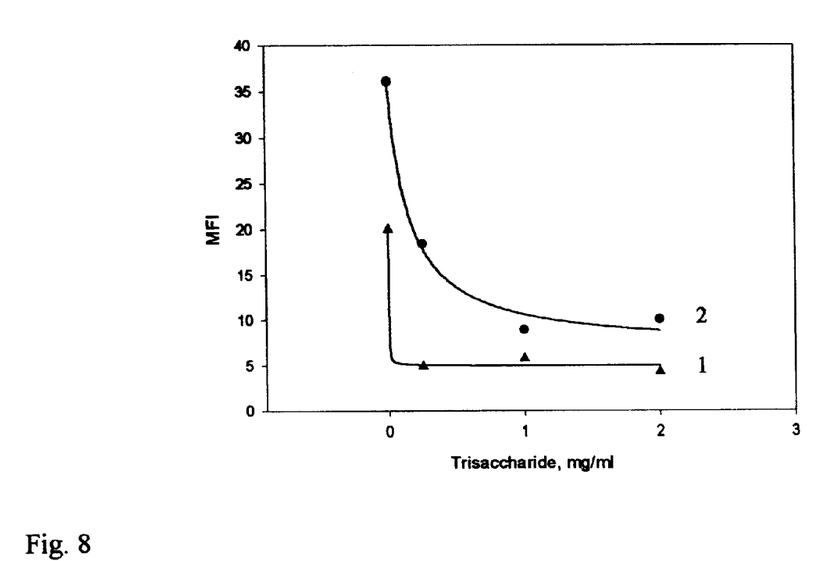

To demonstrate the inhibitory effect of the trisaccharide on IgG or IgM binding to pRBCs, flow cytometry analysis was applied. As shown in FIG. 8, the trisaccharide seemed to inhibit IgG binding more efficiently than IgM binding. In a separate experiment, the S1 fraction was pre-incubated with the trisaccharide at a concentration up to 10 mM. While there was a slight further reduction in MFI for IgM binding, the binding of IgG remained essentially the same when the inhibitor concentration was greater than 1 mM (data not shown). Nevertheless, the binding of both IgG and IgM was still detectable in the presence of 10 mM trisaccharide, strongly suggesting that non-anti-αGal antibodies play a role in binding to pRBCs.

Figure 9:
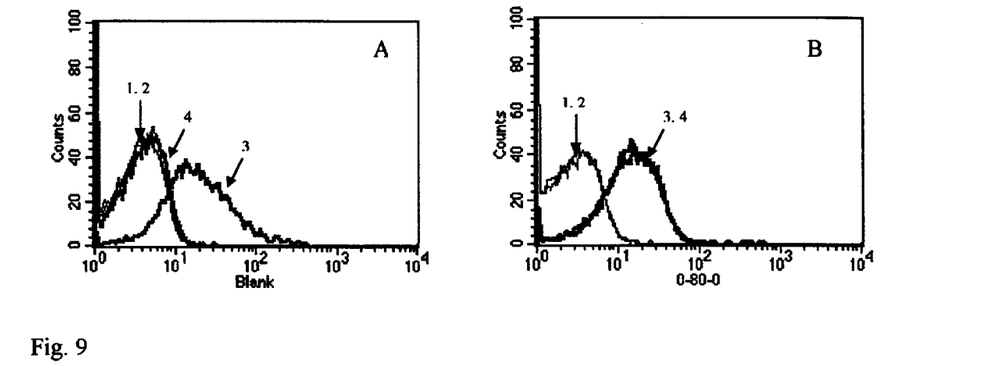
FIGS. 9A and 9B represent the effect of the trisaccharide of FIG. 4 on the binding of anti-αGal and non-αGal antibodies to pRBCs. The control samples (1 and 2) were as described for FIG. 7.

To directly detect non-anti-αGal antibodies from the S2 fraction, we isolated these antibodies by using a pRBC absorption/elution method. The eluted fraction (non-αGal antibodies) was then measured for its binding to pRBCs in the presence or absence of the trisaccharide. As shown in FIG. 9, while the binding of anti-αGal antibodies was completely blocked by 1 mg/ml of the trisaccharide (FIG. 9A), the inhibitor had essentially no effect on the binding of non-anti-αGal antibodies (FIG. 9B). The data clearly suggest that these non-anti-αGal antibodies are naturally present in human serum and interact with certain antigens other than the αGal epitope on pRBCs.

Figure 10:
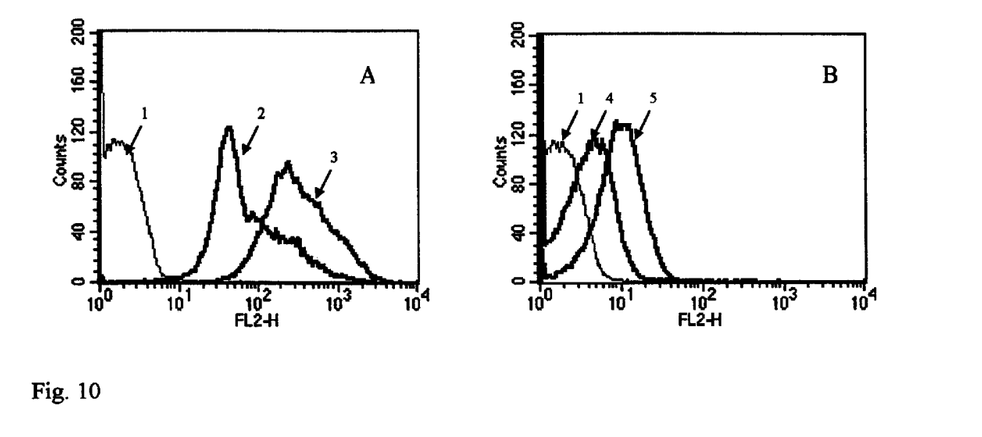
FIGS. 10A and 10B represent the detection of pRBC-bound IgG and IgM by fraction S2 and the non-anti-αGal antibody fraction. PE-conjugated anti-human IgG (or IgM) antibodies were used as the secondary antibodies.

To distinguish between the pRBC-bound IgG and IgM molecules in the S2 and non-αGal fractions, we applied PE-conjugated anti-human IgG (γ chain) or anti-human IgM (μ chain) as the secondary antibody in flow cytometry analysis. As shown in FIG. 10, both types of immunoglobulin are involved in binding to non-αGal epitopes on pRBCs. However, the relative amounts of IgG and IgM in these fractions are difficult to estimate from the graph, since the MFI value is affected by the amount of antibodies used.

Figure 11:
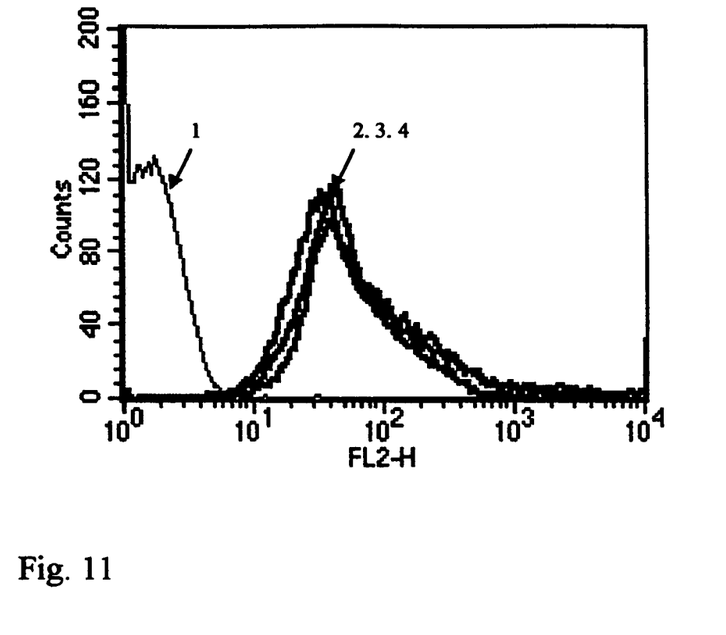
FIG. 11 represents the effect of ssDNA and thyroglobulin on the binding of S2 to pRBCs. The S2 fraction was pre-incubated with ssDNA (2), thyroglobulin (3), or with no inhibitor (3) at 4° C. for 3 hr prior to flow cytometry analyses. Curve 1: negative control lacking the primary and secondary antibodies.

To determine whether the xenoreactive antibodies that we characterized in the binding of pRBCs are polyreactive, we tested the effect of ssDNA and thyroglobulin on binding of antibodies by hemagglutination assays and flow cytometry analyses (Turman M A, Casali P, Notkins A L, Bach F H, and Platt J L (1991) *Transplantation* 52:710–717). To ensure that the xenoreactive antibodies were not present in excess, we titrated the amount of antibodies used in the hemagglutination assays and chose the dilution that produced an intermediate strength (2+ or 3+) for inhibition. Fraction S1 or S2 was pre-incubated with ssDNA or thyroglobulin (final concentration 1 mg/ml) at 4° C. for 3 hr before adding pRBCs for the hemagglutination assay. As shown in Table 2, neither ssDNA nor thyroglobulin showed any inhibitory effect on S1- or S2-induced hemagglutination. To confirm these results, we assessed the binding of xenoreactive antibodies to pRBCs in the presence or absence of ssDNA (or thyroglobulin) by flow cytometry analysis. As shown in FIG. 11, the binding was little affected, if any, by pre-incubation with ssDNA (or thyroglobulin) at 0.01, 0.1 or 1.0 mg/ml (only the last concentration was shown in FIG. 11). Our data suggest that the observed binding of antibodies to pRBCs is not polyreactive in nature.

TABLE 2

| | | Strength | | |
|---|---|---|---|---|
| | | PBS | ssDNA (1 mg/ml) | thyroglobulin (1 mg/ml) |
| S1 | 8 μl | 4 + | | |
| | 4 μl | 3 + | 3 + | 3 + |
| | 2 μl | 1 + | | |

TABLE 2-continued

| | | Strength | | |
|---|---|---|---|---|
| | | PBS | ssDNA (1 mg/ml) | thyroglobulin (1 mg/ml) |
| S2 | 8 μl | 4 + | | |
| | 4 μl | 2 + | 2 + | 2 + |
| | 2 μl | 1 + | | |

5. Isolation of Xenoantigens Recognized by Non-Anti-αGal Antibodies

Although anti-αGal antibody represents the major xenoreactive natural antibody, non-anti-αGal antibodies in human serum have also been suggested to be involved in hyperacute rejection and possibly vascular rejection (Macchiarini P, Oriol R. Azimzadeh A, deMontpreville V, Rieven R, Bevin N, Mizmanian M, and Maartevelle P (1998) *J Thoracic and Cardiovascular Surgery* 116:831–843). However, non-αGal antigens that are recognized by xenoreactive human natural antibodies have not been identified and characterized. Therefore, we isolated non-αGal antigens from pRBCs by using an anti-αGal-depleted serum fraction (S2).

Figure 12:
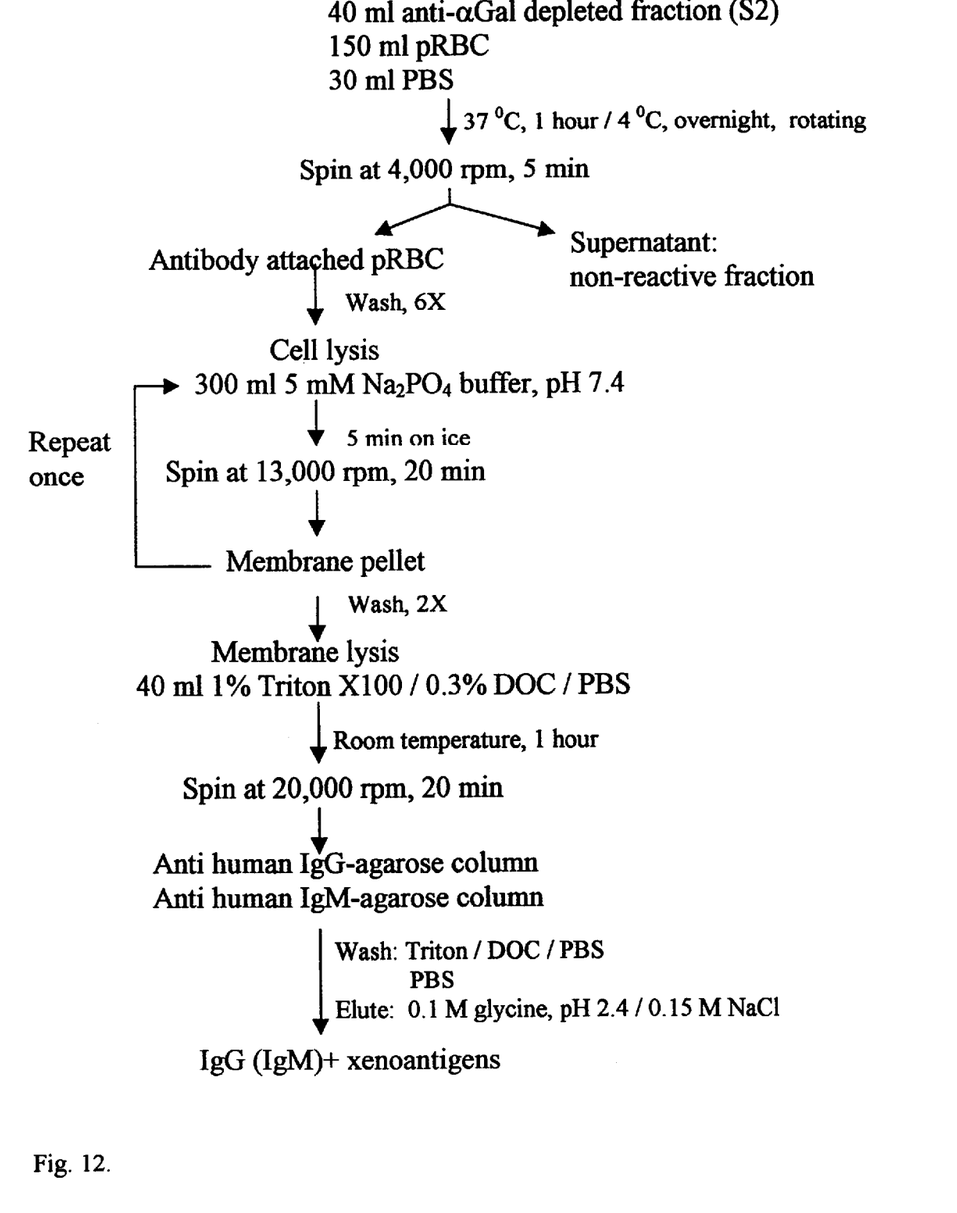
FIG. 12 shows a flow chart of the procedure employed in the isolation of porcine xenoantigens that bind to human non-αGal antibodies.
Figure 13:
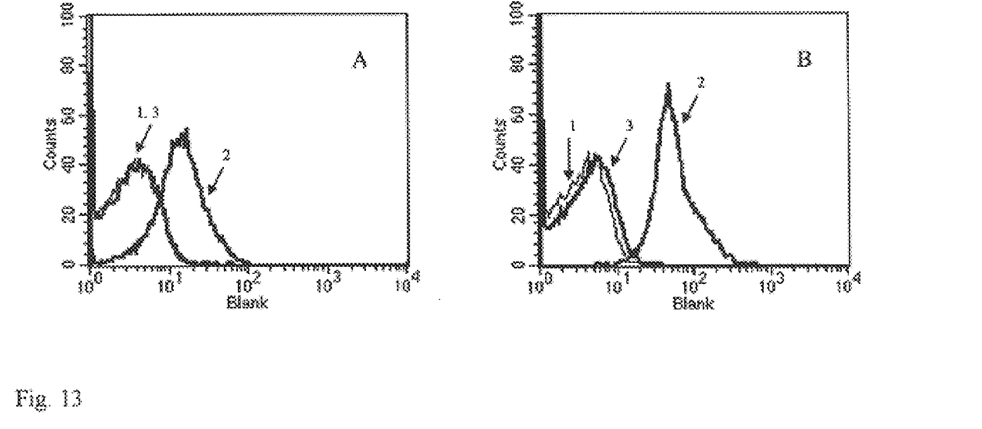
FIGS. 13A and 13B represent the flow cytometry analyses of non-anti-αGal IgG and IgM bound to pRBCs during the isolation of xenoantigens. Samples were incubated at 37° for 1 hr in the absence (2) or presence (3) of pRBCs, followed by incubation at 4° overnight. Thereafter, the samples were analyzed by flow cytometry.

The procedure for the isolation of non-αGal xenoantigens from pRBCs (150 ml of packed cells) is outlined in FIG. 12. To ensure the complete binding of non-anti-αGal antibodies under the conditions applied, the samples from before and after pRBC absorption were analyzed by flow cytometry using both anti-human IgG and anti-human IgM as secondary antibody. As shown in FIG. 13, non-anti-αGal antibodies (both IgG and IgM) were completely absorbed by pRBCs. The final step of the purification involved two affinity columns. The membrane lysate containing immune complexes were first loaded onto the anti-human IgG column. The unbound fraction from the column was then loaded to a second column (anti-human IgM). In this fashion, we were able to separate IgG-bound and IgM-bound xenoantigens.

Figure 14:
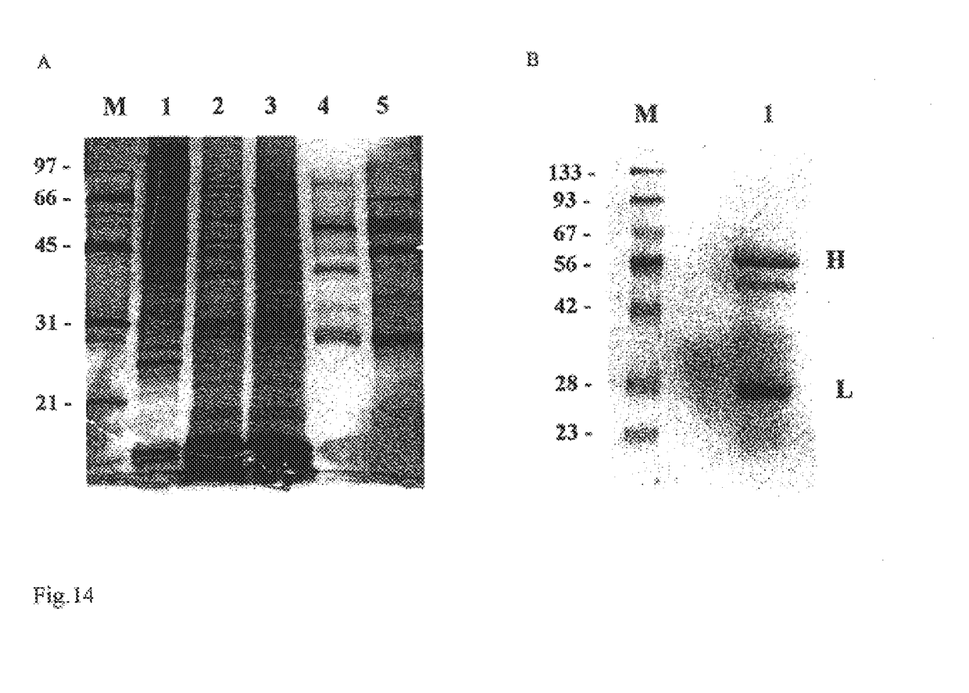
FIGS. 14A and 14B represent SDS-polyacrylamide gel electrophoresis (SDS-PAGE) analysis of pRBC membrane proteins isolated by the procedure of FIG. 12.

Protein samples from different stages of the purification were subjected to SDS-PAGE analysis. As shown in FIG. 14(A), the eluate (lane 6) from the anti-human IgG column consisted of a major band at approximately 45 kDa, and a couple of minor bands in addition to immunoglobulin heavy chain (53 kDa) and light chain (23 kDa). However, the eluate (lane 5) from the anti-human IgM column was too low in protein quantity to carry out further characterization. The 45 kDa protein may represent the major protein antigen on pRBCs that is recognized by non-anti-αGal antibodies (IgG) in human serum. In order to obtain the N-terminal sequence of this novel protein, the eluate from the anti-human IgG column was concentrated and separated by SDS-PAGE. After transfer to a PVDF membrane (FIG. 14(B)), the protein band of 45 kDa was excised for direct sequencing. The N-terminal sequence of this protein was DVXPVESVX (that is, Asp-Val-Xaa-Pro-Val-Glu-Ser-Val-Xaa, wherein Xaa represents any of the 20 amino acids that occur naturally in humans). The 45 kDa protein represents a unique protein, since no homologous proteins in Genbank were identified.

All patents and references mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A purified porcine red blood cell antigen which binds to a xenoreactive human antibody, said antigen not including an α-Gal epitope, and said antigen comprising the amino acid sequence Asp-Val-Xaa-Pro-Val-Glu-Ser-Val-Xaa (SEQ ID NO:1).

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Sus scrofa domestica
<220> FEATURE:
<221> NAME/KEY: VARIANT
<222> LOCATION:
<223> OTHER INFORMATION: Xaa may be any of the 20 amino acids which
      occur naturally in mammals.

<400> SEQUENCE: 1

Asp Val Xaa Pro Val Glu Ser Val Xaa
1               5
```